US009643903B2

(12) United States Patent
Pokrovski et al.

(10) Patent No.: US 9,643,903 B2
(45) Date of Patent: May 9, 2017

(54) CONTINUOUS LOW-TEMPERATURE PROCESS TO PRODUCE TRANS-1-CHLORO-3,3,3-TRIFLUOROPROPENE

(71) Applicant: Honeywell International Inc., Morristown, NJ (US)

(72) Inventors: Konstantin A. Pokrovski, Orchard Park, NY (US); Daniel C. Merkel, West Seneca, NY (US); Hsueh Sung Tung, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 553 days.

(21) Appl. No.: 14/195,893

(22) Filed: Mar. 4, 2014

(65) Prior Publication Data
US 2014/0186230 A1 Jul. 3, 2014

Related U.S. Application Data

(62) Division of application No. 13/220,212, filed on Aug. 29, 2011, now Pat. No. 8,704,017.

(Continued)

(51) Int. Cl.
C07C 17/20 (2006.01)
B01D 3/00 (2006.01)
(Continued)

(52) U.S. Cl.
CPC ............. C07C 17/20 (2013.01); B01D 3/009 (2013.01); C01B 7/0706 (2013.01);
(Continued)

(58) Field of Classification Search
CPC .................................................. B01J 19/1862
See application file for complete search history.

(56) References Cited

U.S. PATENT DOCUMENTS 5,877,359 A 3/1999 Elsheikh
6,013,846 A 1/2000 Wismer et al.
(Continued)

FOREIGN PATENT DOCUMENTS

CN 1224707 A 8/1999
CN 1228403 A 9/1999
(Continued)

OTHER PUBLICATIONS

Extended European Search Report from EPO Appln. No. 11822473.2 dated Mar. 8, 2016.
(Continued)

Primary Examiner — Lessanework Seifu
(74) Attorney, Agent, or Firm — Bruce O. Bradford

(57) ABSTRACT

Disclosed is process for the production of (E) 1-chloro-3,3,3-trifluoropropene (HCFO-1233zd(E)) by conducting a continuous reaction without the use of a catalyst. Also disclosed is an integrated system for producing hydrofluoro olefins, particularly 1233zd(E). The manufacturing process includes six major unit operations: (1) a fluorination reaction of HCC-240fa (in continuous or semi-batch mode) using HF with simultaneous removal of by-product HCl and the product 1233zd(E); (2) recycle of unreacted HCC-240fa and HF together with under-fluorinated by-products back to (1); (3) separation and purification of by-product HCl; (4) separation of excess HF back to (1); (5) purification of final product, 1233zd(E); and (6) isomerization of by-product 1233zd(Z) to 1233zd(E) to maximize the process yield.

6 Claims, 6 Drawing Sheets

Related U.S. Application Data

(60) Provisional application No. 61/379,743, filed on Sep. 3, 2010.

(51) Int. Cl.

| *C01B 7/07* | (2006.01) |
| *C07C 17/25* | (2006.01) |
| *C07C 17/358* | (2006.01) |
| *C07C 17/383* | (2006.01) |
| *C07C 21/18* | (2006.01) |

(52) U.S. Cl.
CPC .......... *C01B 7/0712* (2013.01); *C07C 17/206* (2013.01); *C07C 17/25* (2013.01); *C07C 17/358* (2013.01); *C07C 17/383* (2013.01); *C07C 21/18* (2013.01); *Y02P 20/582* (2015.11)

(56) References Cited

U.S. PATENT DOCUMENTS

| 6,362,382 B1 | 3/2002 | Chen et al. |
| 6,844,475 B1 | 1/2005 | Tung et al. |
| 7,563,936 B2 | 7/2009 | Wang et al. |
| 8,426,656 B2* | 4/2013 | Merkel ................. C07C 17/206 570/156 |
| 2005/0033097 A1 | 2/2005 | Tung et al. |
| 2009/0270661 A1 | 10/2009 | Wang et al. |
| 2010/0152504 A1 | 6/2010 | Hulse et al. |

FOREIGN PATENT DOCUMENTS

| EP | 1277720 A2 | 1/2003 |
| JP | 11-180908 A | 7/1999 |
| WO | 9724307 A1 | 7/1997 |
| WO | 2009003084 A1 | 12/2008 |
| WO | 2010059496 A1 | 5/2010 |
| WO | 2011103035 A2 | 8/2011 |

OTHER PUBLICATIONS

Chinese Office Action in Application No. 201180052870.8, dated Jul. 1, 2014.
Chinese 2nd Office Action in Application No. 201180052870.8, dated Mar. 13, 2015.

* cited by examiner

Reaction Pressure and Temperature profiles that were observed during Experiment 3 in 1-gallon Parr reactor. Reactor was charged with 282.9 grams of HF, and 246.2 grams of 240fa. Exp. #3: No catalyst Reaction Pressure and Temperature profiles that were observed during Experiment 5 in 1-gallon Parr reactor. Reactor was charged with 392.7 grams of HF, and 244.1 grams of 240fa. Exp. #5: No catalyst.

Reaction Pressure and Temperature profiles that were observed during Experiment 4 in 1-gallon Parr reactor. Reactor was charged with 105.7 grams of catalyst TaCl₅, 290.8 grams of HF, and 233.6 grams of 240fa.

CONTINUOUS LOW-TEMPERATURE PROCESS TO PRODUCE TRANS-1-CHLORO-3,3,3-TRIFLUOROPROPENE

CROSS-REFERENCE TO RELATED APPLICATION

This application is a divisional of commonly owned, copending application Ser. No. 13/220,212 filed Aug. 29, 2011, now U.S. Pat. No. 8,704,017. Application Ser. No. 13/220,212 claims domestic priority from commonly owned, U.S. Provisional Patent Application Ser. No. 61/379,743, filed Sep. 3, 2010. The disclosures of these applications are hereby incorporated herein by reference.

FIELD OF THE INVENTION

This invention relates to methods and systems for producing hydrochloro-fluoroolefins, particularly trans-1-chloro-3,3,3-trifluoropropene (HCFO-1233zd (E)).

BACKGROUND OF THE INVENTION

Chlorofluorocarbon (CFC) based chemicals have been widely used in industry in a variety of different applications including as refrigerants, aerosol propellants, blowing agents and solvents, among others. However, certain CFCs are suspected of depleting the Earth's ozone layer. Accordingly, more environmentally friendly substitutes have been introduced as replacements for CFCs. For example, 1,1,1,3,3-pentafluoropropane (HFC-245fa) is recognized as having favorable physical properties for certain industrial applications, such as foam blowing agents and solvents, and therefore is consider to be a good substitute for the CFCs previously used for these applications. Unfortunately, the use of certain hydrofluorocarbons, including HFC-245fa, in industrial applications is now believed to contribute to the global warming. Accordingly, more environmentally friendly substitutes for hydrofluorocarbons are now being sought.

The compound I-chloro-3,3,3-trifluoropropene, also known as HCFO-1233zd or simply 1233zd, is a candidate for replacing HFC-245fa in some applications, including uses as blowing agents and solvents. HCFO-1233zd has a cis or Z-isomer and a trans or E-isomer. Due to differences in the physical properties between these two isomers, pure 1233zd(E), pure 1233zd(Z), or certain mixtures of the two isomers may be suitable for particular applications as refrigerants, propellants, blowing agents, solvents, or for other uses.

Processes for synthesizing 1233zd are known. For example, WO 97/24307 discloses a process for preparing 1233zd via the gas-phase reaction of 1,1,1,3,3-pentachloropropane (HCC-240fa) with hydrogen fluoride (HF). However, this process produces relatively low yields of 1233zd.

U.S. Pat. No. 6,844,475 describes a catalyzed liquid phase reaction of HCC-240fa with HF to produce 1233zd in higher yields. However the presence of the fluorination catalyst promotes the formation of heavy by-products, oligomers, and tars which build up in the reactor over time and lead to catalyst dilution and catalyst deactivation, resulting in loss of productivity due to excessive downtime to remove these by-products from the reactor on a periodic basis.

Known catalytic methods for the production of 1233zd(E) from a liquid phase reaction typically suffer from low yields due to excessive heavies formation caused by the presence of the fluorination catalyst. Accordingly, there remains a need for a process for producing 1233zd(E) in high yields. This invention satisfies that need.

SUMMARY OF THE INVENTION

The present invention solves the problem faced by catalytic reactions for the production of 1233zd(E) by conducting a continuous reaction without the use of a catalyst. One drawback of not using a catalyst is the problem of slower reaction rates. The present invention overcomes this problem by the use of a series of reaction vessels, each vessel in succession converting a portion of the original reactants fed to the lead reactor, with all of the reactors being run simultaneously and in a continuous fashion.

Thus, one embodiment of the invention comprises the following process operations: (1) a series of fluorination reactions of HCC-240fa (in continuous or semi-batch mode) using HF with simultaneous removal of by-product HCl and the product 1233zd(E); (2) optional recycle of unreacted HCC-240fa and HF together with under-fluorinated by-products back to (1); (3) separation and purification of by-product HCl; (4) separation of excess HF back to (1); (5) purification of final product, 1233zd(E); and (6) isomerization of by-product 1233zd(Z) to 1233zd(E) to maximize the process yield.

The number of reactors employed in a train of reactors is determined by their size and the desired production rate. If larger reactors are used, fewer may be required to achieve a desired production rate. If smaller reactors are used, more may be required to achieve a comparable production rate.

As an non-limiting example, the lead reactor converts 70% of the 240fa fed of which only 50% is converted to the desired product while, the rest is only partially fluorinated to intermediates including for example, HCFC-241fa, HCFO-1231zd, HCFC-242fa, HCFO-1232zd and HCFC-243fa. Any unconverted HCC-240fa and under-fluorinated intermediates are high boiling compounds relative to 1233zd(E) and will not easily exit the attached rectifying column.

A continuous stream of unconverted HCC-240fa, under-fluorinated intermediates, and some unreacted HF are taken from the bottom of the reactor and fed to a second reactor. Here more of the original reactants and intermediates are converted to 1233zd(E) which exits the top of the attached rectifying column. Fresh HF may be added as required.

As before, a continuous stream of unconverted HCC-240fa, under-fluorinated intermediates, and some unreacted HF are taken from the bottom of the second reactor and fed to a third reactor where more is converted. Again fresh HF may need to be added. This reactor train continues in series until the desired production rate of 1233zd(E) is achieved.

Another embodiment of the invention provides a method for producing a chlorofluoroalkene comprising the following steps:

(a) providing a liquid reaction admixture comprising hydrogen fluoride, and a reactant composition selected from the group consisting of 1,1,1,3,3-pentachloropropane, 1,1,3,3-tetrachloropropene, 1,3,3,3-tetrachloropropene, and mixtures thereof, wherein the hydrogen fluoride and the reactant composition are present in a molar ratio of greater than about 3:1;

(b) reacting the hydrogen fluoride and the reactant composition in a liquid phase using one or more agitated reactors in series to produce one or more reaction product streams selected from the group consisting of (E) 1-chloro-3,3,3-trifluoropropene, hydrogen chloride, hydrogen fluoride, (Z) 1-chloro-3,3,3-trifluoropropene and unreacted compounds of the reactant composition and/or under fluorinated intermediates, wherein each reaction product stream has a weight ratio of (E) 1-chloro-3,3,3-trifluoropropene to (Z) 1-chloro-3,3,3-trifluoropropene of greater than 1; and (c) optionally, each individual reactor in series can be equipped with a rectifying column that returns some of the unreacted HF, and the majority of unreacted 1,1,1,3,3-pentachloropropane, and/or 1,1,3,3-tetrachloropropene and/or 1,3,3,3-tetrachloropropene and/or under-fluorinated intermediates (e.g., 1,1,3,3-tetrachloro-1-fluoropropane (241fa), 1,1,3,3-tertachloro-3-fluoropropene (1231zd), 1,1,3-trichloro-1,1-difluoropropane (242fa), 1,1,3-trichloro-3,3-difluoropropene (1232zd), 1,1-dichloro-3,3,3-trifluoropropane (243fa) back to the reactor; and (d) combining the one or more resulting reaction product streams into a single combined reaction product stream.

If step (c) is employed then optionally, the method further comprises the following steps (e) and (f), namely:

(e) contacting the combined reaction product stream with a recycle column to produce:

(i) a first crude product stream comprising a majority of the hydrogen chloride, a majority of the (E) 1-chloro-3,3,3-trifluoropropene, optionally a majority of the (Z) 1-chloro-3,3,3-trifluoropropene, and at least a portion of the unreacted hydrogen fluoride, wherein the portion is an amount greater than the amount needed to form an azeotrope with one or more of the (E) 1-chloro-3,3,3-trifluoropropene and the (Z) 1-chloro-3,3,3-trifluoropropene, and (ii) a bottom component comprising a majority of the unreacted hydrogen fluoride and unreacted compounds of the reactant composition and/or under fluorinated intermediates; and (f) returning the bottom component to the reaction admixture.

Note; if step (c) is not employed then steps (e) and (f) are required.

In certain preferred embodiments, the method further comprises one or more of the following additional steps:

(g) separating unreacted reactants, including unreacted 1,1,1,3,3-pentachloropropane, and/or 1,1,3,3-tetrachloropropene and/or 1,3,3,3-tetrachloropropene and/or under-fluorinated intermediates (e.g., 1,1,3,3-tetrachloro-1-fluoropropane (241fa), 1,1,3,3-tertachloro-3-fluoropropene (1231zd), 1,1,3-trichloro-1,1-difluoropropane (242fa), 1,1,3-trichloro-3,3-difluoropropene (1232zd), 1,1-dichloro-3,3,3-trifluoro-propane (243fa),) via distillation and recycling these unreacted reactants and under-fluorinated intermediates back to the reactor; this is achieved either in step (c) or (e), or both;

(h) removing at least a portion, and preferably a majority, of hydrochloric acid by-product via distillation;

(i) separating and recycling unreacted HF in a crude product stream via a sulfuric acid adsorption or a phase separation;

(j) distillation of the crude product stream to separate 1233zd(E) from reaction by-products; and (k) isomerization of 1233zd(Z) by-products to form 1233zd(E).

According to another aspect of the invention, an integrated system for producing a hydrofluoroolefin is provided. This system comprises:

(a) one or more feed streams cumulatively comprising hydrogen fluoride and a reactant composition selected from the group consisting of 1,1,1,3,3-pentachloro-propane, or 1,1,1,3,3-pentachloropropane, and/or 1,1,3,3-tetrachloropropene, and/or 1,3,3,3-tetra-chloropropene;

(b) a liquid phase reactor system consisting of a series (train) of one or more agitated reactors, each fed by its predecessor, and each combined with an optional attached rectifying column (supplied with low-temperature cooling), maintained at a first temperature of about 65° C. to about 175° C., wherein the liquid phase reactor series is fluidly connected to the one or more feed streams;

(c) an optional recycle system comprising a recycle distillation column, a reflux stream fluidly connected to the stripping column, and a combined first crude product stream fluidly connected to the stripping column, wherein the reflux stream is fluidly connected to the lead liquid phase reactor;

Note; if an optional attached rectifying column in step (b) is not employed then step (c) is required.

(d) a hydrogen chloride removal system comprising a first distillation column, a hydrogen chloride by-product stream fluidly connected to the first distillation column, and a second crude product stream fluidly connected to the first distillation column, wherein the first distillation column is fluidly connected to the stripping column;

(e) a hydrogen fluoride recovery system comprising a sulfuric acid absorption and recycle system or a phase separation vessel, a second recycle stream comprising hydrogen fluoride fluidly connected to the sulfuric acid absorption and recycle system or a phase separation vessel;

(f) a third product stream comprising (E) and (Z) 1-chloro-3,3,3-trifluoro-propene fluidly connected to the sulfuric acid absorption and recycle system or a phase separation vessel, wherein the sulfuric acid absorption and recycle system or a phase separation vessel is fluidly connected to the second crude product stream and a 1-chloro-3,3,3-trifluoropropene purification system comprising a second distillation column fluidly connected to the third product stream and (g) a final product stream comprising (E) 1-chloro-3,3,3-trifluoropropene fluidly connected to the second distillation column; a second by-product stream fluidly connected to the distillation column, an isomerization reactor fluidly connected to the second by-product stream; and a product recycle stream fluidly connected to the isomerization reactor and the second distillation column.

DETAILED DESCRIPTION OF THE INVENTION

In preferred embodiments, the invention involves a fully integrated manufacturing process for making (E) 1-chloro-3,3,3-trifluoropropene, as described below.

The reaction chemistry for this process involves a single-step reaction of 1,1,1,3,3-pentachloropropane, or 1,1,1,3,3-pentachloropropane and/or 1,1,3,3-tetrachloro-propene and/or 1,3,3,3-tetrachloropropene mixture with anhydrous HF in a liquid-phase, uncatalyzed agitated reactor to produce primarily (E) 1-chloro-3,3,3-trifluoropropene (1233zd(E)) plus HCl as a by-product. Preferably, the reaction is maintained under conditions (temperature, pressure, residence time) to increase the relative ratio of (E) to (Z) isomers of 1233zd while also minimizing the reaction of HF with the resulting 1233zd(E) which would lead to the formation of HFC-244fa, which in turn can react further to produce HFO-1234ze. Accordingly, the desired reactions involve:

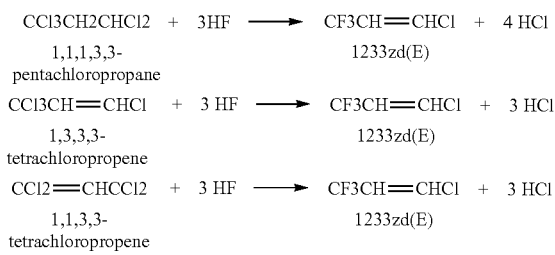

Undesired reactions, which are preferably avoided, include:

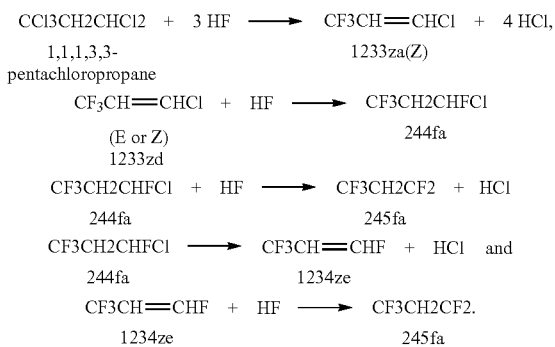

Figure 1:
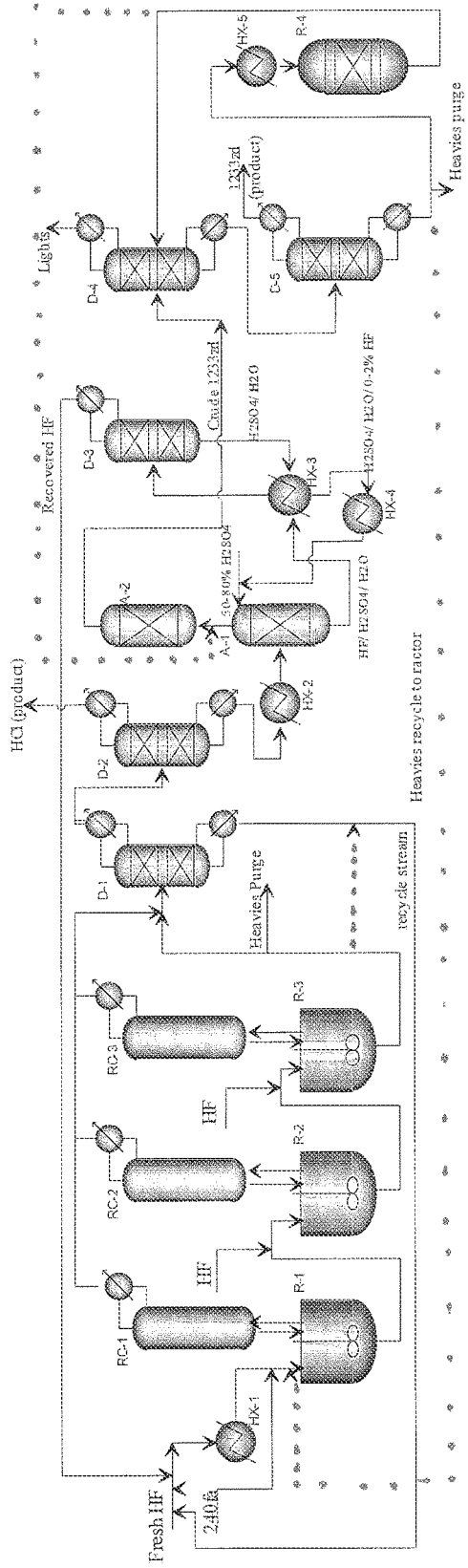
FIG. 1 shows a schematic depiction of processing equipment used in an integrated liquid phase synthesis of 1233zd (E) according to a preferred embodiment of the invention.
Figure 2:
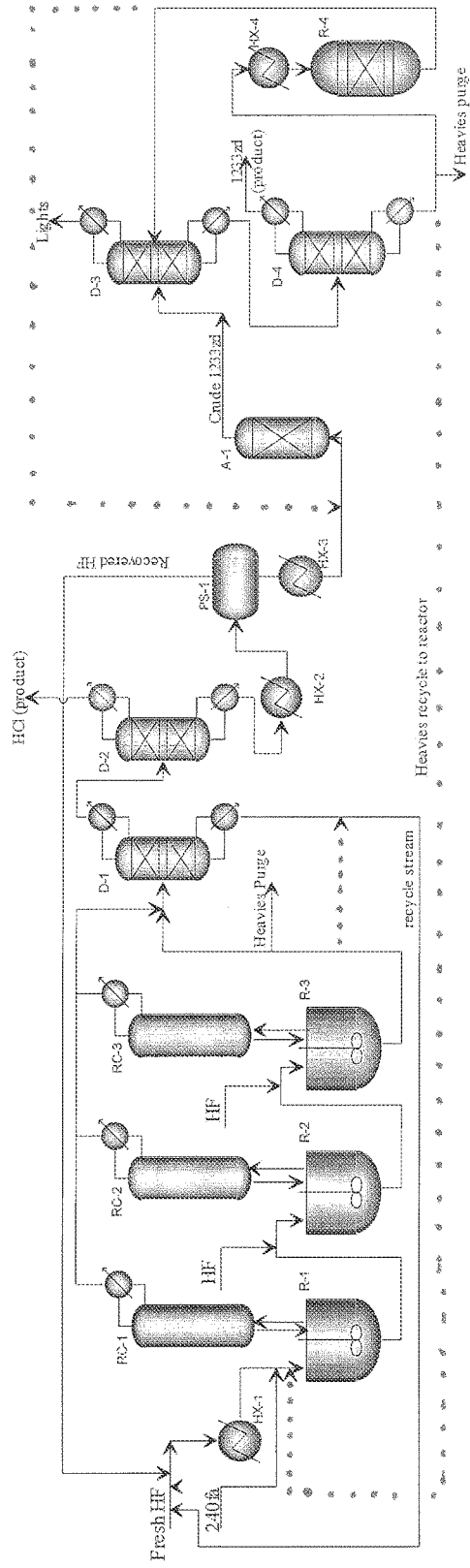
FIG. 2 shows a schematic depiction of processing equipment used in an integrated liquid phase synthesis of 1233zd (E) according to another preferred embodiment of the invention.

In certain embodiments, the manufacturing process comprises six major unit operations. The relative positions of these six operation units are shown in FIGS. 1 and 2. These operation units and/or the reactions therein, comprise:
(1) multiple fluorination reactions of HCC-240fa (in continuous or semi-batch mode) using HF with simultaneous removal of by-product HCl and the product 1233zd(E),
(2) recycle of unreacted HCC-240fa and HF together with under-fluorinated by-products back to (1),
(3) separation and purification of by-product HCl,
(4) separation of excess HF back to (1),
(5) purification of final product, 1233zd(E), and
(6) isomerization of by-product 1233zd(Z) to 1233zd(E) to maximize the process yield.

Reactor and Optional Rectifying Column

Preferably the reactor is constructed from materials which are resistant to the corrosive effects of the HF and HCl, such as Hastelloy-C, Inconel, Monel, Incalloy, or fluoropolymer-lined steel vessels. The reactor is equipped with an agitator. Such liquid-phase fluorination reactors are well known in the art. The reactor is further equipped with an optional rectifying column which permits the desired product to leave (along with by-product HCl, traces of light organics, e.g., principally 1234ze (E+Z), and sufficient anhydrous hydrogen fluoride (AHF) to form azeotropes), while retaining the bulk of the HF, plus under-fluorinated organics.

In preferred embodiments more than one fluorination reactors are connected in a series to increase throughput. In a preferred embodiment, the reaction is conducted in a train of agitated, temperature-controlled reactors, connected in a series and containing liquid reactants. One or more feeds comprising hydrogen fluoride and 1,1,1,3,3-pentachloropropane or 1,1,1,3,3-pentachloropropane and/or 1,1,3,3-tetrachloropropene and/or 1,3,3,3-tetrachloropropene mixture enter the first reactor where they contact each other in a liquid phase. The resulting reaction produces a gas phase product comprising 1233zd(E) as well as various other by-products including HCl and possibly, 1233zd(Z).

The gas phase product leaves the liquid phase reactor and enters an optional integrated rectifying column (operating in reflux mode) which permits the desired product to leave (along with by-product HCl, traces of light organics, e.g., principally 1234ze (E+Z), and anhydrous hydrogen fluoride in the amount greater than that needed to form the azeotropes), while retaining the bulk of the HF, plus under-fluorinated organics. The products exiting the top of the optional rectifying column are fed into HCl recovery system (3). Optionally, the gas phase product leaves the liquid phase reactor and are fed into optional recycle column (2).

The stream of under-fluorinated reaction products and unreacted HCC-240fa and HF is taken from the bottom of the first fluorination reactor and fed together with required amount of fresh HF to the second fluorination reactor that is operated similar to first fluorination reactor. In some embodiments more than two reactors are connected in the series. The stream from the bottom of the last fluorination reactor is optionally fed to the optional recycle column (2) or optionally recycled back to the first reactor (1).

HF and HCC-240fa can be charged to the fluorination reactor and the reaction can be initiated immediately upon heating to the desired reaction temperature while maintaining agitation. The flow of HF to the first fluorination reactor can be resumed, and addition of the 1,1,1,3,3-pentachloropropane or 1,1,1,3,3-pentachloropropane and/or 1,1,3,3-tetrachloropropene and/or 1,3,3,3-tetrachloropropene mixture can be started immediately to cause continuous reaction.

Alternatively, a large amount of the same 1,1,1,3,3-pentachloropropane or 1,1,1,3,3-pentachloropropane and/or 1,1,3,3-tetrachloropropene and/or 1,3,3,3-tetrachloropropene mixture can be added at one time as a batch charge, and then HF can be added gradually to the reactor (a semi-batch operation). Alternatively, a large amount of HF can be added at one time as a batch charge, and then the same 1,1,1,3,3-pentachloropropane or 1,1,1,3,3-pentachloropropane and/or 1,1,3,3-tetrachloropropene and/or 1,3,3,3-tetrachloropropene mixture can be added gradually to the reactor (a semi-batch operation).

In some embodiments utilizing multiple fluorination reactors connected in a series HF can be fed to all of the agitated reactors to maintain proper ratio of HF to organics. Proper temperature control of the coolant and sufficient reflux action are desirable for optimum operation of the rectifying column to be effective. General operating conditions which we have found to work well for the reaction and optional rectifying column are: Operating pressure of 100 to 500 psig maintained by a control valve on the exiting flow from the rectifying column; reactor temperature of 65° C. to 175° C., primarily supplied by steam flow into the reactor jacket; application of −40° C. to 35° C. brine cooling to the heat exchanger on top of the rectifying column to induce reflux; temperature in the center portion of the stripper about 5° C. to 60° C. below that in the reactor; additional heat input by superheating the HF feed with high-pressure steam to 70° C. to 180° C.

It has been discovered that maintaining the reaction under the operating conditions, particularly, a temperature range of 65° C. to 175° C., more preferably 85° C. to 155° C., and most preferably 95° C. to 150° C., produces a high ratio of 1233zd(E) to 1233zd(Z).

Optional Recycle Column

The gaseous stream exiting the top of each of the reactors or optional rectifying columns attached to the fluorination reactors comprising mainly 1233zd(E), 1233zd(Z), HF, and HCl (with some minor components including partially fluorinated intermediates and by-products, over-fluorinated by-products), then enters an optional recycle column or fed into HCl recovery system (3) directly. The stream of unreacted HF and HCC-240fa, under-fluorinated by-products from the bottom of last fluorination reactor is optionally also fed to the recycle column or optionally recycled back to the first reactor (1).

If optional recycle column is employed, a stream comprising mainly unreacted 1,1,1,3,3-pentachloropropane, and/or 1,1,3,3-tetrachloropropene and/or 1,3,3,3-tetrachloropropene, partially fluorinated intermediates, and the majority of the HF exits the bottom of the recycle column and is recycled back to the first liquid phase reactor. Optionally it can be fed to any of the reactor in the series. A stream comprising mainly 1233zd(E), 1233zd(Z), HF, and HCl exits the top of the optional recycle column and enters HCl recovery column.

Removal of HCl

The HCl formed continuously during the reaction is removed from the reactor due to its volatile nature, and flows through the attached distillation column without condensing. The material can then be purified and collected for sale (or further purification) by using a low-temperature HCl distillation column. High purity HCl is isolated and can be absorbed in de-ionized water as concentrated HCl for sale.

Separation and Recycle of Excess HF Back to (1)

The bottoms stream from the HCl removal column (3) that contains crude product mixture of 1233zd(E) and HF (in some embodiments about 30 wt %) is fed to a sulfuric extractor or a phase separator for removal of HF from this mixture. HF is either dissolved in the sulfuric acid or phase separated from the organic mixture. For embodiments utilizing a sulfuric acid adsorption system, the HF is then desorbed from the sulfuric acid/HF mixture by stripping distillation and recycled back to the reactor. For embodiments utilizing a phase separator, HF is phase-separated and recycled back to the reactor. The organic mixture either from the overhead of the sulfuric acid extractor or from the bottom layer of the phase separator may require treatment (scrubbing or adsorption) to remove traces of HF before it is fed to the next unit operation (5).

Purification of Final Product

Purification of final product preferably comprises two continuously operating distillation columns. The first column is used to remove light ends from the 1233zd(E) and the second column is used to remove the heavier components, primarily the 1233zd(Z), which is fed to an isomerization reactor, collected for further use or optionally recycled back to the reactor (2). In certain embodiments, it is desirable to have a purge of heavy by-products from this stream.

Isomerization of by-Product 1233Zd(Z) to 1233Zd(E)

To maximize the 1233zd(E) yield in this process, the by-product 1233zd(Z) formed in the reaction and exiting the bottom of the second column is fed as a vapor to a reactor that contains an isomerization catalyst, preferably fluorinated chromium oxide. Here, the by-product is converted to the desired product. The isomerization reactor exit stream is then recycled to (4) for purification.

In certain preferred embodiments, this step involves controlling the temperature of a heated surface to between 50° C. to 350° C. The heated surface is contacted with the stream containing the 1233zd(Z) by-product. The feed stream is contacted with the heated surface for a period of time sufficient to convert at least a portion of the 1233zd(Z) to 1233zd(E) to produce a product stream rich in 1233zd(E).

In some embodiments, the heated surface includes the inside of a reactor vessel. In addition, or in the alternative, the heated surface may include an outer surface of a packing material, for example a packing material that is packed in a reaction vessel. In some embodiments, the reactor vessel is a batch-wise reactor vessel that can be charged with the feed stream. In some such embodiments, the feed stream may be sealed in the batch-wise reactor, and, after sufficient time passes to isomerize the desired amount of 1233zd(Z), the reactor vessel may be opened to remove the product stream.

In other embodiments, the reactor vessel is a continuous-type reactor vessel, for example a reactor vessel with a first opening and a second opening and a fluid pathway between the first and second openings. The feed stream is fed into the reactor vessel through the first opening and passes through the reactor vessel at a rate sufficient to isomerize the desired amount of 1233zd(Z). The resulting product stream exits the second opening. In one example, the reactor vessel is an elongate reactor vessel (e.g., a Monel™ tube) with the first opening at a first end and the second opening at a second end.

In some embodiments, the reactor vessel may be partially or entirely packed with packing material, for example with a stainless steel packing. In some embodiments, the relatively large surface area of the packing material may facilitate the conversion reaction from the (Z) to the (E) isomer. Support structures that support the packing material may also be disposed in or on the reactor vessel. For example, the packing material may be supported by a mesh or other structure that is disposed under, around, and/or within the packing material. The support structure may comprise the same material as the packing material, e.g., stainless steel (SS), nickel, or any other suitable material.

The packing materials may also comprise one or more catalyst materials. Examples of suitable catalysts for the isomerization of 1233zd are metal oxides, halogenated metal oxides, Lewis acid metal halides, zero-valent metals, as well as combinations of these catalysts. Specific examples of suitable catalysts are AlF3, Cr2O3, fluorinated Cr2O3, zirconium oxide and halogenated versions thereof, or an aluminum oxide and halogenated versions thereof. In addition, the catalysts may be activated prior to use. Examples of activation procedures for several suitable catalysts may be found in U.S. Pat. No. 7,563,936, which is hereby incorporated by reference in its entirety.

Referring to FIG. 1, shown is one embodiment of the equipment used for the synthesis of 1233zd(E) via a liquid phase reaction integrated process utilizing three agitated reactors, equipped with optional rectifying column, connected in series (R-1, R-2, and R-3), having sulfuric acid HF recovery, and optional recycle column after the reactors. Here, liquid phase agitated reactor R-1 is first charged with an required amounts of anhydrous hydrogen fluoride and 1,1,1,3,3-pentachloropropane or 1,1,1,3,3-pentachloropropane and/or 1,1,3,3-tetrachloropropene and/or 1,3,3,3-tetrachloropropene mixture. Preferably the reactor is constructed from materials which are resistant to the corrosive effects of the HF and HCl, such as Hastelloy-C, Inconel, Monel, Incalloy, or fluoropolymer-lined steel vessels. Such liquid-phase fluorination reactors are well known in the art. After the reactor is charged with HF and HCC-240fa an agitator is turned on to achieve a good agitation.

The reaction mixture is then heated to about 85° C. to 150° C. where the fluorination reaction between 1,1,1,3,3-pentachloropropane or 1,1,1,3,3-pentachloropropane and/or 1,1,3,3-tetrachloropropene and/or 1,3,3,3-tetrachloropropene mixture and HF is initiated. Continuous 1,1,1,3,3-pentachloropropane or 1,1,1,3,3-pentachloropropane and/or 1,1,3,3-tetrachloropropene and/or 1,3,3,3-tetrachloropropene mixture and HF (in a stoichiometric excess) feeds are simultaneously fed to heater HX-1 and then into a liquid phase reactor R-1.

Optionally, 1,1,1,3,3-pentachloropropane or 1,1,1,3,3-pentachloropropane and/or 1,1,3,3-tetrachloropropene and/or 1,3,3,3-tetrachloropropene mixture is fed directly into reactor R-1 and not through heater HX-1. The operating pressure of R-1 is in the range 75 psig to 500 psig (preferably 185 psig to 400 psig) is maintained by a control valve on the reactor vapor exit or on the exiting flow from the optional rectifying column RC-1 and the reactor temperature is kept in the range of 65° C. to 175° C. (preferably 100° C. to 140° C.) primarily supplied by steam flow into the reactor jacket. A rectifying column RC-1 is optionally connected to the reactor, R-1, and serves the purpose of knocking down and returning some HF, partially fluorinated intermediates, and some unreacted 1,1,1,3,3-pentachloropropane, 1,1,3,3-tetrachloro-propene or 1,3,3,3-tetrachloropropene back to the reactor for further reaction.

The stream exiting the top of the reactor or the top of the optional rectifying column RC-1 (if it is employed) comprising mainly 1233zd(E), 1233zd(Z), HF, and HCl (with some minor components including partially fluorinated intermediates and by-products, and over-fluorinated by-products), then enters optional recycle column D-1. If optional rectifying column RC-1 is employed the optional recycle column D-1 can be omitted.

When the desired level in the first fluorination reactor is achieved a stream of unreacted HF, unreacted 1,1,1,3,3-pentachloropropane, 1,1,3,3-tetrachloropropene or 1,3,3,3-tetrachloropropene, and under-fluorinated intermediates is fed to second fluorination reactor R-2. The feed of fresh HF is also fed to R-2 to maintain proper HF to organics ratio. The second reactor R-2 is operated similar to R-1 and can be equipped with optional rectifying column RC-2 that is operated similar to RC-1. Reactor R-2 is maintained at temperature 115° C. to 150° C. and pressure of about 170 psig to 425 psig.

The stream exiting the top of the reactor R-2 or the top of the optional rectifying column RC-2 (if it is employed) comprising mainly 1233zd(E), 1233zd(Z), HF, and HCl (with some minor components including partially fluorinated intermediates and by-products, and over-fluorinated by-products), then enters then enters optional recycle column D-1. If optional rectifying column RC-2 is employed the optional recycle column D-1 can be omitted.

When the desired level in the second fluorination reactor is achieved a stream of unreacted HF, unreacted 1,1,1,3,3-pentachloropropane, 1,1,3,3-tetrachloropropene or 1,3,3,3-tetrachloropropene, and under-fluorinated intermediates is fed to third fluorination reactor R-3. The feed of fresh HF is also fed to R-3 to maintain proper HF to organics ratio. Reactor R-3 is operated similar to R-1 and R-2 and can be equipped with optional rectifying column RC-3 that is operated similar to RC-1 and RC-2. Reactor R-3 is maintained at temperature 125° C. to 160° C. and pressure of about 160 psig to 450 psig.

The stream exiting the top of the reactor R-3 or the top of the optional rectifying column RC-3 (if it is employed) comprising mainly 1233zd(E), 1233zd(Z), HF, and HCl (with some minor components including partially fluorinated intermediates and by-products, and over-fluorinated by-products), then enters then enters optional recycle column D-1. If optional rectifying column RC-3 is employed the optional recycle column D-1 can be omitted.

When the desired level in the third fluorination reactor is achieved a stream of unreacted HF, unreacted 1,1,1,3,3-pentachloropropane, 1,1,3,3-tetrachloropropene or 1,3,3,3-tetrachloropropene, and under-fluorinated intermediates is optionally fed to the recycle column D-1 or recycled back to the first reactor R-1 via vaporizer HX-1. Optionally, this stream can be combined directly with the bottoms recycle stream from optional recycle stream D-1 back to reactor R-1 via vaporizer HX-1. Optionally, heavy by-products are removed from this stream by establishing a small heavies purge continuous or intermittent side stream.

The optional recycle column D-1 is operated in a such a way that a stream comprising mainly unreacted 1,1,1,3,3-pentachloropropane, and/or 1,1,3,3-tetrachloropropene and/or 1,3,3,3-tetrachloropropene, partially fluorinated intermediates, and the majority of the HF exits the bottom of the recycle column and is recycled back to the liquid phase reactor R-1 via vaporizer HX-1. A stream comprising mainly 1233zd(E), 1233zd(Z), HF, and HCl exits the top of the recycle column and enters HCl column D-2. A stream comprising mainly HCl by-product exits the top of the HCl column and is fed to an HCl recovery system. The recovered HCl by-product can be sold for profit. The HCl column bottoms stream consisting mainly of 1233zd(E), 1233zd(Z), and HF are then fed into an HF recovery system.

The HF recovery system starts with the crude 1233zd/HF stream being vaporized in heat exchanger HX-2 and fed into HF absorption column A-1. Here a liquid stream of 50% to 80% H2SO4 contacts the gaseous 1233zd/HF stream and absorbs the majority of the HF. The stream exiting the bottom of A-1 comprises HF/H2SO4/H2O and is fed to heat exchanger HX-3 where it is heated to a temperature sufficient to flash the majority of the HF along with small amounts of H2O and H2SO4. This stream is fed to HF recovery distillation column D-2. The liquid remaining after the HF is flashed off in HX-3 consisting mainly of H2SO4 and H2O (with 0% to 2% HF) is cooled in HX-4 and recycled back to HF absorption column A-1. The HF recovery column, D-3, bottoms stream comprising mainly H2SO4 and H2O are recycled back to heat exchanger HX-3.

Anhydrous HF is recovered from the top of the HF recovery column, D-3, and is recycled back to the reactor R-1 via vaporizer HX-1. The stream exiting the top of HF absorption column A-1 comprising mainly 1233zd(E) and 1233zd(Z) (trace HF) is sent forward to a polishing system A-2 where the gaseous stream contacts a water or a caustic solution to remove trace HF and is subsequently dried with a desiccant. Acid free crude product exiting absorber A-2 is sent to the first of two purification columns, D-4.

A stream exiting the top of the column D-4 consists mainly of reaction by-products that have boiling points lower than that of 1233zd(E). The stream exiting the bottom of lights column D-4 consisting mainly of 1233zd(E) and 1233zd(Z) and heavier by-products is fed to product recovery distillation column D-5. Product grade 1233zd(E) exits the top of the column to product storage. The product column bottoms consist mainly of 1233zd(Z) and reaction by-products with boiling points higher than that of 1233zd (E) is then fed to vaporizer HX-5 and then to isomerization reactor R-4 where by-product 1233zd(Z) is converted to the desired product. The stream leaving R-4 is then recycled to lights distillation column D-4 for purification.

Optionally, if any by-products in the stream entering R-4 are unstable they may decompose and form small amounts of HF or HCl. In this case the stream exiting R-4 can be recycled and combined with the stream entering the polishing system A-2 to remove the acid. Optionally, the stream exiting the bottom of the product recovery distillation column, D-5 can be recycled back to first liquid phase reactor R-1. In any of these options a heavies purge stream from the bottom of the product recovery distillation column, D-5, will be required to prevent build-up of high boiling impurities in the purification system. The heavies purge stream is collected for later use or waste disposal.

Referring to FIG. 2, shown is one embodiment of equipment used in the synthesis of 1233zd(E) via a liquid phase reaction integrated process utilizing three reactors, equipped with optional rectifying column, connected in series (R-1, R-2, and R-3), having a phase separation HF recovery system, and optional recycle column after the reactor. Here, liquid phase reactor R-1 is first charged with an required amounts of anhydrous hydrogen fluoride and 1,1,1,3,3-pentachloropropane or 1,1,1,3,3-pentachloro-propane and/or 1,1,3,3-tetrachloropropene and/or 1,3,3,3-tetra-chloropropene mixture. Preferably the reactor is constructed from materials which are resistant to the corrosive effects of the HF and HCl, such as Hastelloy-C, Inconel, Monel, Incalloy, or fluoro-polymer-lined steel vessels. Such liquid-phase fluorination reactors are well known in the art. After reactor is charged with HF and HCC-240fa an agitator is turned on to achieve a good agitation.

The reaction mixture is then heated to about 85° C. to 150° C. where the fluorination reaction between 1,1,1,3,3-pentachloropropane or 1,1,1,3,3-pentachloropropane and/or 1,1,3,3-tetrachloropropene and/or 1,3,3,3-tetrachloropropene mixture and HF is initiated. Continuous 1,1,1,3,3-pentachloropropane or 1,1,1,3,3-pentachloropropane and/or 1,1,3,3-tetrachloropropene and/or 1,3,3,3-tetrachloropropene mixture and HF (in a stoichiometric excess) feeds are simultaneously fed to heater HX-1 and then into a liquid phase reactor R-1.

Optionally, 1,1,1,3,3-pentachloropropane or 1,1,1,3,3-pentachloropropane and/or 1,1,3,3-tetrachloropropene and/or 1,3,3,3-tetrachloropropene mixture is fed directly into reactor R-1 and not through heater HX-1. The operating pressure of R-1 is in the range 75 psig to 500 psig (preferably 185 psig to 400 psig) is maintained by a control valve on the exiting flow from the top of the reactor R-1 or optional rectifying column RC-1 and the reactor temperature is kept in the range of 65° C. to 175° C. (preferably 100° C. to 140° C.) primarily supplied by steam flow into the reactor jacket. A rectifying column RC-1 is optionally connected to the reactor, R-1, and serves the purpose of knocking down and returning some HF, partially fluorinated intermediates, and some unreacted 1,1,1,3,3-pentachloropropane, 1,1,3,3-tetrachloro-propene or 1,3,3,3-tetrachloropropene back to the reactor for further reaction.

The stream exiting the top of the reactor or the top of the optional rectifying RC-1 (if it is employed) comprising mainly 1233zd(E), 1233zd(Z), HF, and HCl (with some minor components including partially fluorinated intermediates and by-products, and over-fluorinated by-products), then enters optional recycle column D-1. If optional rectifying column RC-1 is employed the optional recycle column D-1 can be omitted.

When the desired level in the first fluorination reactor is achieved a stream of unreacted HF, unreacted 1,1,1,3,3-pentachloropropane, 1,1,3,3-tetrachloropropene or 1,3,3,3-tetrachloropropene, and under-fluorinated intermediates is fed to second fluorination reactor R-2. The feed of fresh HF is also fed to R-2 to maintain proper HF to organics ratio. The second reactor R-2 is operated similar to R-1 and can be equipped with optional rectifying column RC-2 that is operated similar to RC-1. Reactor R-2 is maintained at temperature 115° C. to 150° C. and pressure of about 170 psig to 425 psig.

The stream exiting the top of the reactor R-2 or the top of the optional rectifying column RC-2 (if employed) comprising mainly 1233zd(E), 1233zd(Z), HF, and HCl (with some minor components including partially fluorinated intermediates and by-products, and over-fluorinated by-products), then enters then enters recycle column D-1. If optional rectifying column RC-2 is employed the optional recycle column D-1 can be omitted.

When the desired level in the second fluorination reactor is achieved a stream of unreacted HF, unreacted 1,1,1,3,3-pentachloropropane, 1,1,3,3-tetrachloropropene or 1,3,3,3-tetrachloropropene, and under-fluorinated intermediates is fed to third fluorination reactor R-3. The feed of fresh HF is also fed to R-3 to maintain proper HF to organics ratio. Reactor R-3 is operated similar to R-1 and R-2 and can be with optional rectifying column RC-3 that is operated similar to RC-1 and RC-2. Reactor R-3 is maintained at a temperature of 125° C. to 160° C. and pressure of about 160 psig to 450 psig.

The stream exiting the top of the reactor R-3 or the top of the optional rectifying column RC-3 (if employed) comprising mainly 1233zd(E), 1233zd(Z), HF, and HCl (with some minor components including partially fluorinated intermediates and by-products, and over-fluorinated by-products), then enters then enters recycle column D-1. If optional rectifying column RC-3 is employed the optional recycle column D-1 can be omitted.

When the desired level in the third fluorination reactor is achieved a stream of unreacted HF, unreacted 1,1,1,3,3-pentachloropropane, 1,1,3,3-tetrachloropropene or 1,3,3,3-tetrachloropropene, and under-fluorinated intermediates is optionally fed to the recycle column D-1 or recycled back to the first reactor R-1 via vaporizer HX-1. Optionally, this stream can be combined directly with the bottoms recycle stream from optional recycle stream D-1 back to reactor R-1 via vaporizer HX-1. Optionally, heavy by-products are removed from this stream by establishing a small heavies purge continuous or intermittent side stream.

The recycle optional column D-1 is operated in a such a way that a stream comprising mainly unreacted 1,1,1,3,3-pentachloropropane and/or 1,1,3,3-tetrachloropropene and/or 1,3,3,3-tetrachloropropene, partially fluorinated intermediates, and the majority of the HF exits the bottom of the recycle column and is recycled back to the liquid phase reactor R-1 via vaporizer HX-1. A stream comprising mainly 1233zd(E), 1233zd(Z), HF, and HCl exits the top of the recycle column and enters HCl column D-2. A stream comprising mainly HCl by-product exits the top of the HCl column and is fed to an HCl recovery system. The recovered HCl by-product can be sold for profit.

The HCl column bottoms stream consisting mainly of 1233zd(E), 1233zd(Z), and HF are then fed into an HF recovery system. The HF recovery system starts with the 1233zd/HF stream being fed into heat exchanger HX-2 where it is pre-cooled to temperatures below 0° C. and then enters phase separation vessel PS-1. Here the stream temperature is maintained or further cooled to −40° C. to 0° C. The HF rich top layer (less than 10% 1233zd) is recycled back to the liquid phase reactor R-1.

The organic rich bottom layer containing mainly 1233zd (less than 4% HF) is sent to vaporizer HX-3 and then forward to a polishing system A-1 where the gaseous stream contacts water or a caustic solution to remove trace HF and is subsequently dried with a desiccant. Acid free crude product exiting absorber A-1 is sent to the first of two purification columns, D-3. A stream exiting the top of the column D-3 consists mainly of reaction by-products that have boiling points lower than that of 1233zd(E).

The stream exiting the bottom of lights column D-3 consisting mainly of 1233zd(E) and 1233zd(Z) and heavier by-products is fed to product recovery distillation column D-4. Product grade 1233zd(E) exits the top of the column to product storage. The product column bottoms consist mainly of 1233zd(Z) and reaction by-products with boiling points higher than that of 1233zd(E) is then fed to vaporizer HX-4 and then to isomerization reactor R-4 where by-product 1233zd(Z) is converted to the desired product. The stream leaving R-4 is then recycled to lights distillation column D-3 for purification. Optionally, if any by-products in the stream entering R-4 are unstable they may decompose and form small amounts of HF or HCl.

In this case the stream exiting R-4 can be recycled and combined with the stream entering the polishing system A-1 to remove the acid. Optionally, the stream exiting the bottom of the product recovery distillation column, D-4 can be recycled back to first liquid phase reactor R-1. In any of these options a heavies purge stream from the bottom of the product recovery distillation column, D-4, will be required to prevent build-up of high boiling impurities in the purification system. The heavies purge stream is collected for later use or waste disposal.

The following examples are provided to further illustrate the invention and should not be taken as limitations of the invention.

Example 1

As part of the development of a liquid phase process for making 1233zd(E) an experiment was run using no catalyst. The experiment used a one gallon agitated Parr reactor and was run in a batch mode. The experiment was called Exp #3. For the experiment 282.9 grams of HF and 246.2 grams of HCC-240fa (1,1,1,3,3-pentachloro-propane) (12.4 to 1 mole ratio HF:240fa) were charged to the reactor at room temperature. The mixer was then turned on ensuring the reactor contents were well mixed. Then the reactor was heated to the desired temperature. Upon heating the pressure began to rise as HCl by product was produced as a result of a fluorination reaction. The reactor was heated to about 110° C. over several hours and held. The pressure was controlled in the range of 250 psig to 325 psig by venting off the HCl generated in the reaction to a dry-ice trap (DIT).

At the completion of the reaction after about 9.5 hrs., (determined by lack of HCl generation), the pressure from the reactor was vented into the DIT. The crude product from the DIT was transferred into a 1 L Monel absorption cylinders (frozen in dry-ice) with about 400 grams of water. The absorption cylinder was allowed to warm up to room temperature and a sample of an organic layer that had formed in the cylinder (aqueous and organic layers were present in the cylinder upon discharge) was taken and analyzed by gas chromatography (GC). GC results showed 4.48 GC % 245fa, 90.61 GC % 1233zd(E), 0.22 GC % 244fa, 2.93 GC % 1233zd(Z). The amount of organic collected was later quantified by further analysis of the different phases and amounted to 75.4 grams.

The organic remaining in the reactor after venting was recovered by quenching the reactor with about 300 to 400 grams of water to absorb HF and HCl, and then adding about 100 grams of carbon tetrachloride. The reactor was then opened and its contents discharged into a plastic bottle. The organic was separated from the aqueous phase by use of a reparatory funnel. The amount of heavies collected from the reactor was calculated by subtracting the weight of CCl4 added to the reactor from the total weight of organic phase collected and amounted to 96.9 grams. GC/MS and GC analysis of the organic layer followed and revealed 3 distinct peaks attributed to under-fluorinated species HCFC-241fa, 91.057 GC %, HCFC-242fa, 0.760 GC %, and the starting material HCC-240fa, 8.183 GC %.

Figure 3:
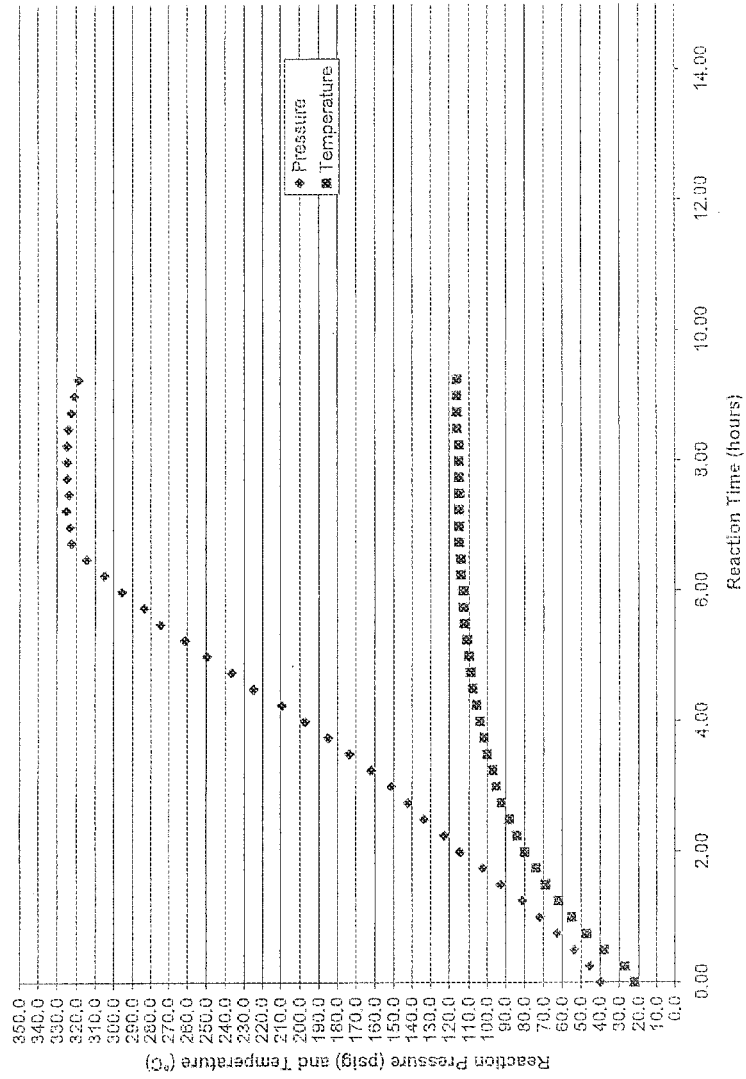
FIG. 3 illustrates the reaction pressure and temperature profiles that were observed during Experiment 3 (no catalyst) in a one gallon Parr reactor.

Experimental conditions and results of GC analysis of the reaction products are presented in FIG. 3 and Table I below.

TABLE I

| Charged to reactor | Weight (moles) |
|---|---|
| HF | 282.9 grams (14.145 moles) |
| 240fa | 246.2 grams (1.138 moles) |
| Collected reaction products | Weight |
| Volatile products form DIT | 75.4 grams (4.48 GC % 245fa, 90.61 GC % 1233zd(E), 0.22 GC % 244fa, 2.93 GC % 1233zd(Z)) |
| Heavies from reactor | 96.9 grams (0.760 GC % G-242, 91.057 GC % G-241, 8.183 GC % G-240fa) |

Example 2

The experiment described in Example 1 was repeated using the same equipment and procedure. The reactor was heated to 110° C. and held. However, the experiment was not allowed to go to completion. The experiment was called Exp #5. After about 6.5 hrs. the reactor pressure reached 320 psig and the experiment was stopped. 382.7 grams of HF and 244.1 grams of HCC-240fa were initially charged to the reactor. Results are similar to those of Example 1, but with a lower conversion of HCC-240fa.

Figure 4:
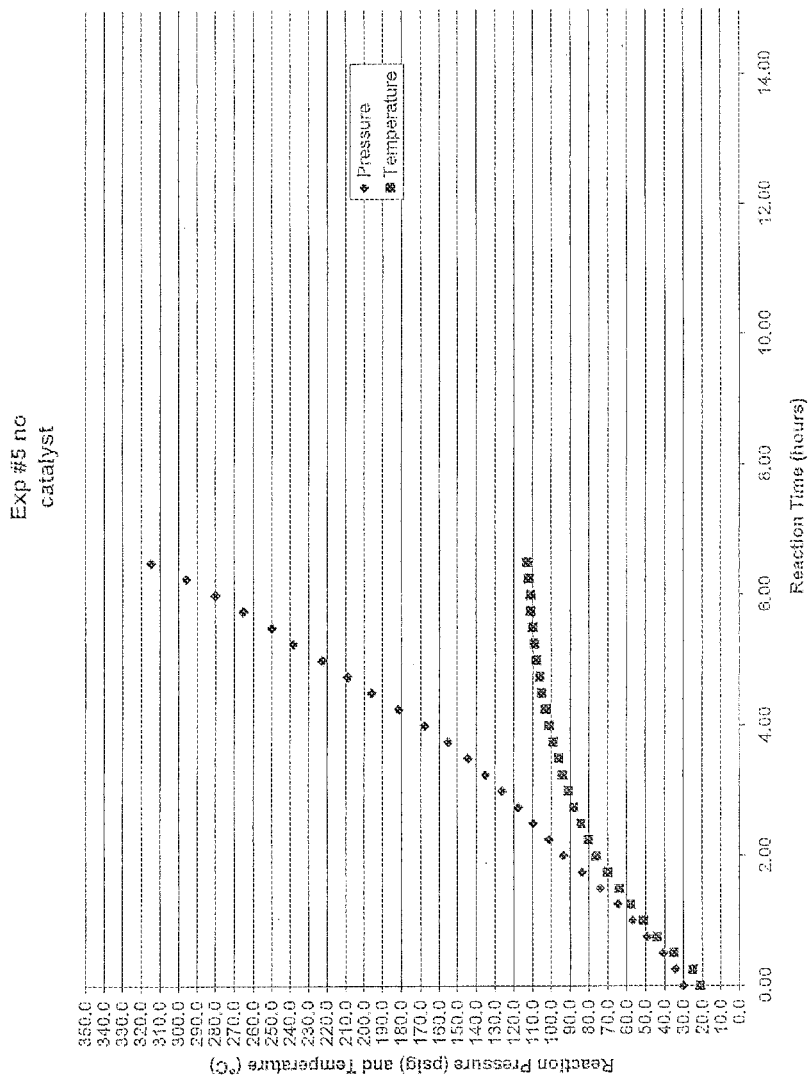
FIG. 4 illustrates the reaction pressure and temperature profiles that were observed during Experiment 5 (no catalyst) in a one gallon Parr reactor.

Experimental conditions and results of GC analysis of the reaction products are presented in the FIG. 4 and Table II below.

TABLE II

| Charged to reactor | Weight (moles) |
|---|---|
| HF | 392.7 grams (16.485 moles) |
| 240fa | 244.1 grams (1.129 moles) |
| Collected reaction products | Weight |
| Volatile products form DIT | 76.1 grams (5.66 GC % 245fa, 88.90 GC % 1233zd(E), 1.12 GC % 244fa, 2.75 GC % 1233zd(Z)) |
| Heavies from reactor | 121.4 grams (1.713 GC % G-242, 58.691 GC % G-241, 39.596 GC % G-240fa) |

Comparative Example 1

As part of the development of a liquid phase process for making 1233zd(E) an experiment was run using a fluorination catalyst. The experiment used the same one gallon agitated Parr reactor as described in Examples 1 and 2 and was run in a batch mode and was called Exp #4. The empty reactor was first charged with 105.7 grams of TaCl5 liquid fluorination catalyst. Then 290.8 grams of HF was charged into the reactor at room temperature which was immediately followed by a pressure rise in the reactor due to the generation of HCl as the catalyst became fluorinated.

After venting the pressure (HCl) resulting from the reaction of HF with the catalyst, 233.6 grams of HCC-240fa was charge to reactor. The mixer was then turned on ensuring the reactor contents were well mixed. Then the reactor was heated to the desired temperature. Upon heating the pressure began to rise as HCl by product was produced as a result of a fluorination reaction. The pressure was controlled in the range of 200 psig to 230 psig by venting off the HCl generated in the reaction to a dry-ice chilled trap (DIT). The reactor was held at 60° C. to 80° C. for about 8.5 hours (note the lower temperature required when using a catalyst).

The volatile reaction products collected in the DIT and the reactor residue were worked up and analyzed the same way as described in Example 1. The volatile reaction products were the same as those from the experiments run without catalyst described in Examples 1 and 2, but the organic remaining in the reactor after venting were different. This time the organic layer (CCl4 with dissolved organic) was a dark brown color and was much more viscous than the organic layer collected in the non-catalytic experiments and GC analysis indicated the presence of multiple oligomeric by-products and tars. No HCC-240 or under-fluorinated species, HCFC-241fa and HCFC-242fa, were present.

Figure 5:
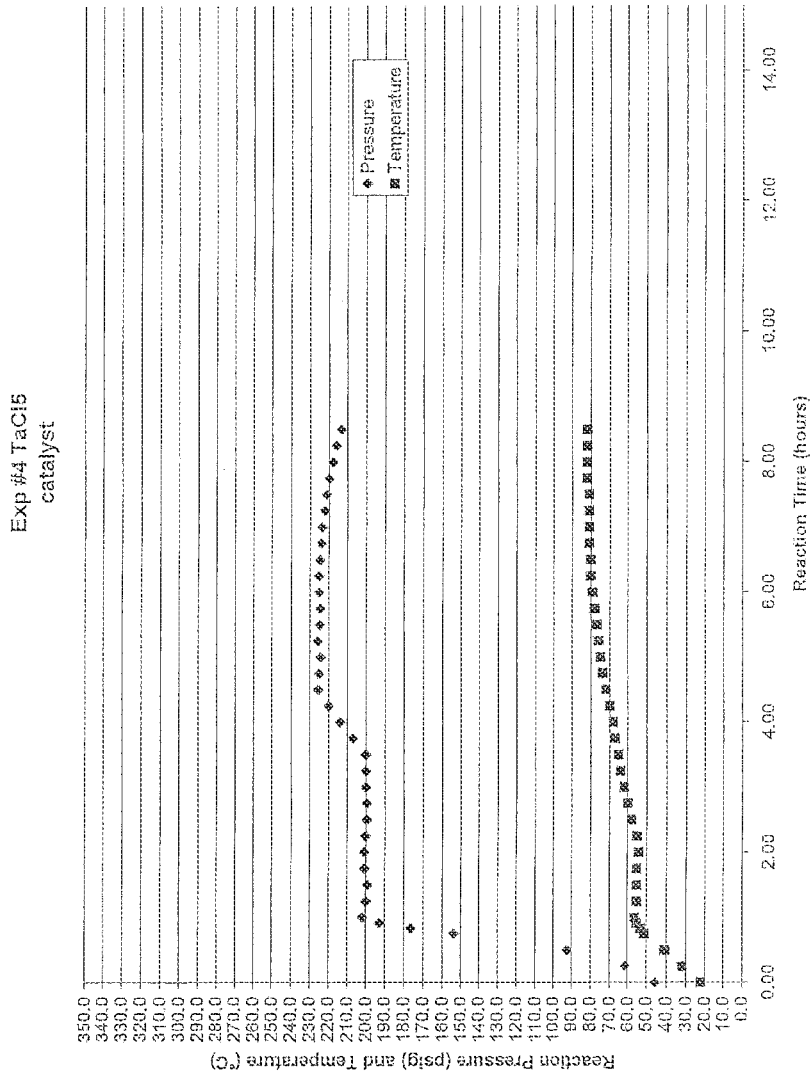
FIG. 5 illustrates the reaction pressure and temperature profiles that were observed during Experiment 4 (catalyst) in a one-gallon Parr reactor.

Experimental conditions and results of GC analysis of the reaction products are presented in the FIG. 5 and Table III below.

TABLE III

| Collected reaction products | Weight (moles) |
|---|---|
| TaCl5 | 105.7 grams (0.295 moles) |
| HF | 290.8 grams (14.54 moles) |
| 240fa | 233.6 grams (1.08 moles) |
| Collected reaction products | Weight |
| Volatile products form DIT | 94.0 grams |
| | (39.28 GC % 245fa, 4.50 GC % 1233zd(E), |
| | 42.67 GC % 244fa, 2.93 GC % 1233zd(Z)) |
| Heavies from reactor | 48.3 grams (multiple oligomers) |

Comparative Example 2

The experiment described in Comparative Example 1 is repeated using the same equipment and procedure. This time the fluorination catalyst is TiCl4. Results are similar to those of Comparative Example 1 with the formation of multiple oligomers and tars that are left in the reactor at the completion of the experiment.

Example 3

This example illustrates the initial reactor running in continuous mode. Experiments were performed in a 1-gallon agitated Parr reactor equipped with 2"-ID×8-feet column filled with ¼" ProPak packing and a tube-in-tube condenser. The reactor was heated by external 1.5 kW electric heater and the condenser was cooled by water. Reactor pressure was controlled by venting reactor products to caustic scrubber (1 Owt % KOH circulating at 55° C.) and then collecting in a chilled product collection cylinder. 240fa was fed to the vapor space of the reactor and HF was fed via dip-tube to the bottom of the reactor to facilitate mixing of the reactants.

Prior to start-up, the empty reactor was charged with 3 lbs of HF. 240fa feed was introduced at 0.62 lbs/hr after the reactor was heated to about 105° C. Introduction of 240fa feed resulted in a pressure increase in the reactor indicating the initiation of the fluorination reaction and formation of HCl. 2.5 hours after 240fa feed was introduced into the reactor pressure reached 400 psig with the corresponding reactor temperature of 139° C. The steady collection rate was achieved after about 1 to 2 hours at the reaction pressure. Then HF feed was introduced into the reactor at the rate 0.3 to 0.6 lbs/hr in order to maintain the reactor weight. Reaction system parameters are presented in FIG. 6. The reaction was stopped after 48 hours on-stream. The reactor contents were sampled and no organics was found in the reactor. During 48 hours of the reaction we accumulated about 2 additional lbs of HF. The excess HF was vented to the scrubber bringing the HF inventory in the reactor to 3 lbs.

Then the reaction was re-started at 400 psig pressure. The reactor was heated to about 107° C. and 240fa feed was started at 0.6 lbs/hr and after about 2.5 hours the reactor temperature reached 140° C. and reaction pressure stabilized at 400 psig. For first 30 hours of the reaction the 240fa feed rate was maintained at 0.6 lbs/hr and HF feed rate was maintained at 0.4 lbs/hr. The reactor temperature was about 139° C. to 140° C. and the temperature at the top of the column was about 117° C. to 120° C. Then 240fa feed rate was increased to 0.8 lbs/hr and HF feed rate was increased to 0.6 lbs/hr. This resulted in the reactor temperature decrease by about 1° C. The product collection rate increase almost immediately after 240fa feed rate was increased.

After 48 hours on-stream the 240fa feed rate was increased to 1.0 lbs/hr and HF feed rate was increased to about 0.7 lbs/hr. Again product collection rate increased almost immediately after feed rates were increased. The reactor weight stayed constant. At about 72 hours on-stream 240fa feed rate was further increased to 1.25 lb/hr and HF feed rate was increased to about 0.85 lb/hr to maintain reactor weight. Once again product collection rate increased almost immediately after feed rates were increased. The reactor temperature stabilized at about 137.5° C. and temperature at the top of the column stabilized at about 115° C. to 118° C. The 240fa and HF feed were stopped after 79 hours on-stream. About 10 minutes after feeds were stopped system pressure started to decrease and reactor started to warm up indicating the completion of the reaction.

Figure 6:
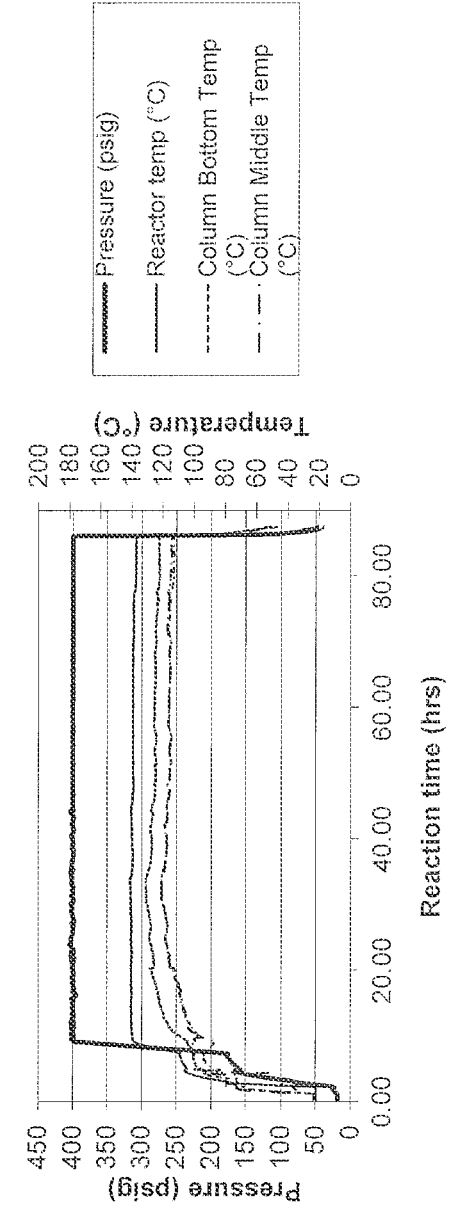
FIG. 6 illustrates the reactor system conditions observed during the experiment described in Example 3.

Reaction system parameters are presented in FIG. 6 and the analysis of the reaction products at different feed rates presented in the Table IV below. At 240fa feed rate of 1.25 lb/hr and HF feed rate of 0.85 lb/hr residence time is estimated at 3.2±0.5 hours (assumptions: reaction volume=1 gallon, at 140° C. HF density=5.1lb/gallon and 240fa density=8.2 lb/gallon).

TABLE IV

Effect of feed rate (residence time) on the reaction products
HF rich conditions, 1-gallon RXR, HF: 240fa = 8-10:1 (in the feed)
T = 137° C. to 140° C., P = 400 psig)

| Compound | 240fa feed rate 0.6 lb/hr | 240fa feed rate 0.8 lb/hr | 240fa feed rate 1.25 lb/hr |
|---|---|---|---|
| 1234ze(E) | 3.8491 | 2.6980 | 2.5470 |
| 245fa | 0.1998 | 0.1585 | 0.1563 |
| 1234ze(Z) | 0.4205 | 0.3441 | 0.3141 |
| 1233zd(E) | 84.7453 | 86.2050 | 88.5162 |
| 244fa | 1.3306 | 0.6375 | 0.4912 |
| 1233zd(Z) | 3.6456 | 3.9272 | 3.6307 |
| 1232zd | 0.8892 | 0.2372 | 0.1260 |
| 243fa | 2.2687 | 1.0104 | 0.5738 |
| 242fa | 2.5730 | 4.5663 | 3.3162 |
| 241fa | 0.0050 | 0.1237 | 0.2326 |
| Usable products | 89.5919 | 91.9054 | 92.6387 |
| Over fluorinated by-products and cis-1233zd | 10.4081 | 8.0946 | 7.3613 |
| Apparent Residence time | 6 hours | 4.5 hours | <3 hours |

Example 4

A series of three continuously stirred reactors with attached rectifying columns is used to produce crude 1233zd (E) crude product. There is a bottom drain on the first reactor that feeds the second reactor and a drain on the second reactor that feeds the third reactor. The overhead stream that exits each of the three rectifying columns are connected to combine all 1233zd(E) crude and HCl produced and fed forward for separation into individual components.

To the lead reactor is continuously fed a 15:1 mole ratio of HF:HCC-240fa. The reactor temperature is maintained at about 140° C. The reactor pressure is controlled at about 400 psig. HF, HCl, and crude 1233zd(E) exit the top of the attached rectifying column continuously. The reactor is drained continuously to the $2^{nd}$ reactor at a rate that maintains a near constant level in the reactor. The lead reactor achieves a 70% conversion of HCC-240fa and a yield of 50% of 1233zd(E) crude. The organic composition of the material being drained to the $2^{nd}$ reactor is about 40% HCC-240fa, 55% HCFC-241fa, and 5% HCFC242fa. HF is also present in this stream. Fresh HF is added to the $2^{nd}$ reactor to make up for rectifier column overhead losses.

The second reactor is run at a 375 psig and is maintained at 135° C. HF, HCl, and crude 1233zd(E) exit the top of the attached rectifying column continuously. The second reactor is drained continuously to the third reactor at a rate that maintains a near constant level in the reactor. The second reactor achieves a 90% conversion of HCC-240fa and a yield of 70% of 1233zd(E) crude. The organic composition of the material being drained to the second reactor is about 33% HCC-240fa, 62% HCFC-241fa, and 5% HCFC242fa. HF is also present in this stream. Fresh HF is added to the $3^{rd}$ to make up for rectifier column overhead losses.

The third reactor is run at a 350 psig and is maintained at 130° C. HF, HCl, and crude 1233zd(E) exit the top of the attached rectifying column continuously. The third reactor is drained continuously to a recycle column at a rate that maintains a near constant level in the reactor. The third reactor achieves a 100% conversion of HCC-240fa and a yield of 95% of 1233zd(E) crude. The organic composition of the material being drained to the recycle column is about 95% HCFC-241fa, and 5% HCFC-242fa. HF is also present in this stream.

Example 5

This example illustrates the recovery of anhydrous HF from a mixture of HF and HCFO-1233zd according to certain preferred embodiments of the present invention.

A mixture consisting of about 70 wt. % HCFO-1233zd(E) crude and about 30 wt. % HF is vaporized and fed to the bottom of a packed column at a feed rate of about 2.9 lbs per hour for about 4 hours. A stream of about 80 wt. % sulfuric acid (80/20 H2SO4/H2O) with about 2% HF dissolved therein is fed continuously to the top of the same packed column at a feed rate of about 5.6 lbs per hour during the same time frame. A gaseous stream exiting the top of the column comprises HCFO-1233zd(E) crude with less than 1.0 wt. % HF therein. The concentration of HF in the sulfuric acid in the column bottoms increases from 2.0 wt. % to about 15 wt. %.

The column bottoms containing sulfuric acid and about 15 wt. % HF is collected and charged into a two gallon Teflon® vessel. The mixture is heated to about 140° C. to vaporize and flash off HF product, which is collected. The collected HF product contains about 6000 ppm water and 500 ppm sulfur. The sulfuric acid contains about 500 ppm of TOC (total organic carbon).

The HF collected from flash distillation is distilled in a fractionation distillation column and anhydrous HF is recovered. The recovered anhydrous HF contains less than 50 ppm of sulfur impurities and less than 100 ppm water.

Example 6

This example demonstrates the purification of the acid free 1233zd(E) crude product. About 92 lbs of acid free 1233zd crude material produced in Example 2 was charged to a batch distillation column. The crude material contained about 94 GC area % 1233zd(E) and 6 GC area % impurities. The distillation column consisted of a ten gallon reboiler, two inch inner diameter (ID) by ten feet propack column, and a shell and tube condenser. The column had about 30 theoretical plates. The distillation column was equipped with temperature, pressure, and differential pressure transmitters. About 7 lbs of a lights cut was recovered which consisted of mainly 1234ze (Z+E), trifluoropropyne, 245fa, and 1233zd(E). 82 lbs of 99.8+GC area % 1233zd(E) were collected. The reboiler residue amounting to about 3 lbs was mainly 244fa, 1233zd(Z), 1233zd dimmer, and 1233zd(E). The recovery of 99.8+GC area % pure 1233zd(E) was 94.8%.

Example 7

This example demonstrates the use of the optional recycle column. A representative 1233zd(E) liquid phase reactor effluent mixture as determined in Example 2 is charged into a batch distillation column. The distillation column consists of a ten gallon reboiler, two inch ID by ten feet propack column, and a shell and tube condenser with −40° C. coolant flow capability. The column has about 30 theoretical plates. The distillation column is equipped with temperature, pressure, and differential pressure transmitters. The distillation column feed mixture is about 30 wt % HF, 37 wt % HCl and 33% 1233zd(E) crude. The distillation is run at a pressure of about 100 psig and a differential pressure (delta P) of 15 to 20 inches of water. Both the distillate and reboiler are sampled periodically and analyzed for organic, HF, and HCl using gas and ion chromatography.

Initially, HCl, organic, and HF are observed in both samples. As more material is removed as distillate the concentration of the reboiler changes. First, the concentration of HCl decreases until it is undetectable. The distillation is allowed to proceed until the concentration of organic in the reboiler sample decreases to only trace amounts as analyzed using gas chromatography. At the conclusion of the distillation the material remaining in the reboiler is essentially pure HF. The recovered HF (reboiler bottoms) is then used to demonstrate recycle of recovered HF back to the liquid phase fluorination reactor and works satisfactorily.

Example 8

This example demonstrates the HF recovery by phase separation. It was visually observed using a Teflon® cylinder that HF and 1233zd(E) form a heterogeneous mixture. The phase-separation of a mixture containing 1233zd(E) and HF was performed in the temperature range of −20° C. to +0° C. A 500 ml stainless steel (SS) sample cylinder was used for the study. The temperature of the cylinder was controlled with ethanol circulating through the coil wrapped around the cylinder. A thermocouple was attached to the outside wall of the cylinder (between cooling coil and the cylinder wall) and positioned in the middle of the cylinder to measure the temperature. The SS cylinder was also equipped with sampling valves at the bottom and the top of the cylinder.

To the SS cylinder is charged about 50 g of anhydrous HF and 50 g of a crude 1233zd(E). The weight ratio HF:1233zd(E) was about 1:1. The mixture was allowed to cool down to the desired temperature for 60 minutes and then the contents of the separator were mixed. The mixture was allowed to phase separate for 60 minutes and then samples of the bottom and top layers were taken. The samples of the top and bottom layers were absorbed in distilled water and HF concentration was determined by titration with 0.1 N KOH of the acidic aqueous phase. The results of the experiments are presented in the Table V.

TABLE V

Effect of the separator temperature on the phase separation of HF/crude 1233zd(E) mixture.

| | Separator temperature | | |
|---|---|---|---|
| | −20° C. | −10° C. | 0° C. |
| HF | 53.2 g | 49.6 g | 53.5 g |
| Crude 1233zd(E) | 58.9 g | 50.5 g | 47.3 g |
| Bottom layer | 40.6 g | 30.0 g | 23.5 g |
| HF in bottom layer | 2.7% | 2.0% | 4.2% |
| Top layer | 71.5 g | 70.1 g | 77.3 g |
| Organics in top layer | 28.4% | 32.1% | 34.7% |

Example 9

This example demonstrates the isomerization of 1233zd(Z) into desired product 1233zd(E). Conversion of 1233zd(Z) into 1233zd(E) was performed using a Monel™ reactor (ID two inch, length 32 inch) equipped with a Monel™ preheater (ID one inch, length 32 inch) which was filled with Nickel mesh to enhance heat transfer. The reactor was filled with 1.5 L of pelletized fluorinated Cr2O3 catalyst. Nickel mesh was placed at the top and at the bottom of reactor to support the catalyst. A multi-point thermocouple was inserted at the center of the reactor.

A feed containing about 10.0 wt % 1233zd(E) and 86.3 wt % 1233zd(Z) was introduced into the reactor at the rate of 0.7 lb/hr. The feed was vaporized prior to entering the reactor preheater. The reactor temperature for this experiment was varied between 100° C. and 200° C. The temperature gradient throughout the reactor never exceeded 3° C. to 5° C. Samples of reaction products were taken every hour and GC analysis of those samples is given in Table VI.

TABLE VI

| Reaction | Area Percent by GC | | |
|---|---|---|---|
| Temperature ° C. | 1233zd(E) | 1233zd(Z) | Others |
| Initial | 10.0 | 86.3 | 3.7 |
| 103 | 69.6 | 27.9 | 2.5 |
| 104 | 69.8 | 27.9 | 2.4 |
| 128 | 70.2 | 27.6 | 2.2 |
| 128 | 65.0 | 32.8 | 2.2 |
| 128 | 62.8 | 35.0 | 2.2 |
| 128 | 60.9 | 36.9 | 2.2 |
| 151 | 60.8 | 37.1 | 2.1 |
| 151 | 61.8 | 36.2 | 2.0 |
| 151 | 62.4 | 35.6 | 2.0 |
| 151 | 58.9 | 39.0 | 2.1 |
| 181 | 62.2 | 35.8 | 2.0 |
| 199 | 68.3 | 29.4 | 2.3 |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. An integrated system for producing (E)1-chloro-3,3,3-trifluoropropene, wherein the system comprises:
   (a) one or more feed streams cumulatively comprising hydrogen fluoride and a reactant composition selected from the group consisting of 1,1,1,3,3-pentachloropropane, or 1,1,1,3,3-pentachloropropane, and/or 1,1,3,3-tetrachloropropene, and/or 1,3,3,3-tetrachloropropene;
   (b) a liquid phase reactor system consisting of a series of one or more agitated reactors, each fed by its predecessor, and wherein the liquid phase reactor series is fluidly connected to the one or more feed streams;
   (c) recycle system comprising a recycle distillation column, a reflux stream fluidly connected to the top of the reactor and a combined first crude product stream fluidly connected to the top of the reactor, wherein the reflux stream is fluidly connected to a liquid phase reactor in the series;
   (d) a hydrogen chloride removal system comprising a first distillation column, a hydrogen chloride by-product stream fluidly connected to the first distillation column, and a second crude product stream fluidly connected to the first distillation column, wherein the first distillation column is fluidly connected to a stripping column;
   (e) a hydrogen fluoride recovery system comprising a sulfuric acid absorption and recycle system or a phase separation vessel, a second recycle stream comprising hydrogen fluoride fluidly connected to the sulfuric acid absorption and recycle system or a phase separation vessel;
   (f) a third product stream comprising (E) and (Z) 1-chloro-3,3,3-trifluoro-propene fluidly connected to the sulfuric acid absorption and recycle system or a phase separation vessel, wherein the sulfuric acid absorption and recycle system or a phase separation vessel is fluidly connected to the second crude product stream and a 1-chloro-3,3,3-trifluoropropene purification system comprising a second distillation column fluidly connected to the third product stream and (g) a final product stream comprising at least 50 wt. percent (E)1-chloro-3,3,3-trifluoropropene fluidly connected to the second distillation column; a second by-product stream fluidly connected to the distillation column, an isomerization reactor fluidly connected to the second by-product stream; and a product recycle stream fluidly connected to the isomerization reactor and the second distillation column.

2. The integrated system of claim 1, wherein one or more of the reactors in part (b) is combined with an attached rectifying column supplied with low-temperature cooling, and maintained at a temperature of about 65° C. to about 175° C.

3. The integrated system of claim 1, wherein the separating and recycling of HF is accomplished by phase separation.

4. The integrated system of claim 1, wherein each reactor is maintained at a temperature range of 65° C. to 175° C.

5. The integrated system of claim 1, wherein each reactor is maintained at a temperature range of 85° C. to 170° C.

6. The integrated system of claim 1, wherein each reactor is maintained at a temperature range of 95° C. to 160° C.

* * * * *